United States Patent [19]

Ramsbotham et al.

[11] 4,345,060
[45] Aug. 17, 1982

[54] DIGLYCIDYL ETHERS OF DIPHENYLOL ALKANES, THEIR PREPARATION AND USE IN CURABLE COMPOSITIONS

[75] Inventors: John Ramsbotham; Johan van Gogh, both of Amsterdam, Netherlands

[73] Assignee: Shell Oil Company, Houston, Tex.

[21] Appl. No.: 273,704

[22] Filed: Jun. 15, 1981

[30] Foreign Application Priority Data

Jul. 8, 1980 [GB] United Kingdom ............... 8022299

[51] Int. Cl.$^3$ ............................................. C08G 59/22
[52] U.S. Cl. ................................. 528/103; 528/87; 528/106; 528/112; 528/121; 549/517
[58] Field of Search .............. 260/348.64, 348.15; 528/87, 112, 121; 528/106, 103

[56] References Cited

U.S. PATENT DOCUMENTS

| | | | |
|---|---|---|---|
| 2,506,486 | 5/1950 | Bender et al. | 260/47 |
| 2,633,458 | 3/1953 | Shokal | 260/45.2 |
| 2,841,595 | 7/1958 | Pezzaglia | 260/348.64 X |
| 3,477,990 | 11/1969 | Dante et al. | 260/47 |
| 4,273,915 | 6/1981 | Soula et al. | 260/348.15 X |

Primary Examiner—Earl A. Nielsen
Attorney, Agent, or Firm—Norris E. Faringer

[57] ABSTRACT

Diglycidyl ethers are prepared from a mixture of isomers of 1,1-bis(hydroxyphenyl)heptane. The diglycidyl ethers have low viscosity and good compatibility with aliphatic hydrocarbon solvents; they can be cured with the usual curing agents for epoxy resins, e.g., polyamines, and can be used in solventless coating compositions.

5 Claims, No Drawings

DIGLYCIDYL ETHERS OF DIPHENYLOL ALKANES, THEIR PREPARATION AND USE IN CURABLE COMPOSITIONS

FIELD OF THE INVENTION

The invention relates to novel diglycidyl ethers of diphenylol alkanes, to their preparation and to their use in curable compositions, for example, in combination with amino compounds, for use in coatings, castings, adhesives, mortars, and related applications.

BACKGROUND OF THE INVENTION

Diglycidyl ethers of 2,2-bis(4-hydroxyphenyl)propane (abbreviated DPP or Bisphenol A or BPA) of a large variety in molecular weights are well-known commercial products. They are also known as epoxy resins, and find use on a large scale as main resinous components in curable or thermosetting compositions.

General reference to such epoxy resins is made in the books: "Handbook of Epoxy Resins" by Henry Lee and Kris Neville, dated 1967, and "Uses of Epoxy Resins" by W. G. Potter, dated 1975, as well as in a multitude of issued patents, such as, for example U.S. Pat. No. 2,633,458.

These epoxy resins are compounds having the general formula:

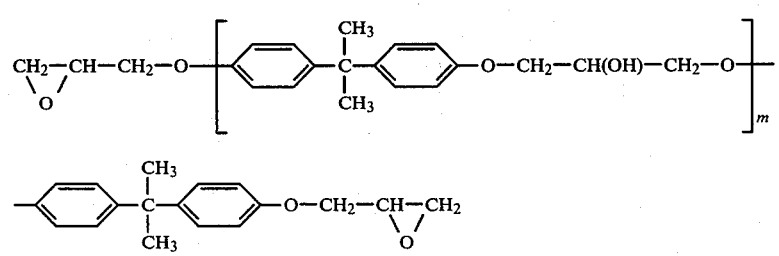

wherein m is a number having an average value from 0 to 12. Compounds of the above formula wherein m is 0 to 1 are liquid or semiliquid at room temperature, compounds wherein m is at least 2 are solids at room temperature.

For some purposes, however, some properties of epoxy resins from DPP need improvement. For example, the viscosity of the liquid resins is rather high, usually 10 Pa.s (25° C.) or more. When a resin of lower viscosity is required, the DPP-based resin has to be diluted with a small amount of a reactive diluent, as, for example, a mono-epoxide or di-epoxide of low viscosity and other structure, usually a glycidyl ether of a monohydric alcohol or a glycol. These additives, however, will usually reduce the resistance of the cured products to heat, solvents, and/or chemicals.

Further, the glycidyl ethers of DPP have low compatibility for aliphatic hydrocarbons (which are attractive as cheap solvents), and have to be dissolved or diluted with the more expensive polar solvents, such as ketones, glycol ethers or glycol esters.

For some purposes, a better flexibility of cured products is required. This can be obtained by use of flexibilizers (non-reactive), flexibilizing epoxides, and/or flexibilizing curing agents. Apart from price considerations (the additives are usually more expensive) there is usually a reduction in other useful properties, such as resistance to heat, solvents, and/or chemicals.

Summarizing, there is still a need for epoxy resins of the bisphenol type, having good compatibility with aliphatic hydrocarbon solvents, and providing the usual curing agents cured products of improved flexibility, without undue reduction in adhesion, hardness, and resistance to heat and chemicals, whereas the liquid resins of that type should have a low viscosity.

SUMMARY OF THE INVENTION

The invention provides novel epoxy resins meeting these requirements. The novel epoxy resins are defined as diglycidyl ethers of isomeric diphenylol alkanes, the glycidyl ethers having the formula:

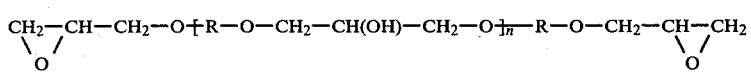

(II)

wherein n is a number of from 0 to 4, R is the group

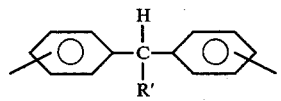

and R' is n-hexyl, the weight ratio of para,para'-isomer to ortho-para'-isomer being from about 80:20 to about 40:60.

DESCRIPTION OF THE PREFERRED EMBODIMENT

Preferred are the liquid diglycidyl ethers, wherein n has an average value of from 0 to 1 in the above-noted generalized structural formula II. These liquids have a low viscosity, have no tendency to crystallize, and can be easily diluted with aliphatic hydrocarbon solvents. These liquid epoxy resins can be prepared in high yields by reaction of the corresponding mixture of bisphenol isomers with epichlorohydrin, or dichlorohydrin, and an alkali metal hydroxide, if desired in the presence of catalysts or solvents.

The mixture of bisphenol isomers can be prepared in high yield by reaction of n-heptanal with a molar excess of phenol in the presence of hydrochloric acid, if desired, in the presence of mercapto co-catalysts, at moderate temperatures. The excess of phenol and the catalyst can be removed after the reaction, as for example, by distillation. The product, the residue, is a mixture of bisphenol isomers, containing mainly p,p'-isomer and o,p'-isomer (in a weight ratio of from 80:20 to 40:60), and may contain up to 10% by weight of higher condensates (trihydric phenols). The weight ratio p,p'-isomer to o,p'-isomer is usually from 65:35 to 55:45, and the amount of o,o'-isomer can normally be neglected.

At room temperature and slightly above, these mixtures of bisphenol isomers are liquid to semi-solid, and can be diluted easily with solvent or reagent required for conversion into glycidyl ethers. For the latter reaction there is no need to separate the isomers, or to enrich the content of one of the isomers, although that may be desirable under certain circumstances.

The mixture of bisphenol isomers can, for example, be diluted easily with epichlorohydrin and/or alcohols, such as methanol, ethanol, n-propanol, isopropanol, n-butanol, isobutanol, and sec.-butanol.

The mixture of bisphenol isomers can be converted into diglycidyl ethers by reaction with epichlorohydrin and an alkali metal hydroxide, by the methods well known for the preparation of diglycidyl ethers of 2,2-bis(4-hydroxyphenyl)propane.

The liquid new epoxy resins can be prepared in general by reacting the bisphenol with a molar excess of epichlorohydrin, if desired first in a pre-reaction in the presence of a catalyst-promoting formation of chlorohydrin ethers, whereafter the equivalent amount, or preferably an excess, of alkali metal hydroxide is added in one or more stages for dehydrohalogenation.

So-called solid diglycidyl ethers (wherein n in the above formula (II) is at least 2) can be prepared by reacting the mixture of bisphenol isomers in aqueous medium with less than the equivalent amount of epichlorohydrin and with alkali metal hydroxide in one stage. Similar products can also be prepared by a fusion reaction of the liquid diglycidyl ether with a calculated amount (underdose) of the same bisphenol in the presence of a small amount of a catalyst, for example, a tertiary amine, a quaternary ammonium salt, or a quaternary phosphonium salt, as for example, described in U.S. Pat. No. 3,477,990. Other types of "solid" diglycidyl ethers can be prepared by a fusion reaction of liquid diglycidyl ethers according to the invention, in the presence of a catalyst as referred to above, with a different bisphenol, for example with 2,2-bis(4-hydroxyphenyl)propane.

The diglycidyl ethers according to the invention can be modified by reaction with all types of modifying agents known for the usual epoxy resins, for example, with fatty acid to prepare epoxy resin esters, with amines (excess) to prepare soluble epxoy resin/amine adducts, with dicarboxylic acids (underdose) to prepare epoxy resins having a dicarboxylic acid ester group in the chain.

Diglycidyl ethers according to the invention can be converted to hard resinous materials by mixing and reacting with an epoxy resin curing agent. Useful curing agents are amino compounds having at least two amino hydrogen atoms per molecule. Examples are aliphatic polyamines, aromatic polyamines, soluble adducts thereof with mono-epoxides and/or di-epoxides, amino amides derived from aliphatic polyamines and carboxylic acids, heterocyclic polyamines. The cure with amino compounds may be accelerated by phenols or monocarboxylic acids. Other useful curing agents are polycarboxylic acids and polycarboxylic acid anhydrides; the cure may be accelerated by small amounts of catalysts, such as tertiary amines, for example benzyldimethylamine, or 2,4,6-tris(dimethylaminomethyl)-phenol, stannous salts, and others. By way of illustration only, examples of suitable catalysts are disclosed in U.S. Pat. No. 3,477,990.

Solvents, diluents, extenders (coal tar, asphaltic bitumen), fillers, and pigments may also be added, depending on the intended use. Diglycidyl ethers according to the invention wherein n has a value from 0 to 1 can be used as main binder components in coating compositions, in particular, for solventless coatings, or for use in civil engineering, for example, for coverage of floors, road surfaces, bridge decks, as adhesive, or for casting, moulding, laminating, for example for electrical applications.

Diglycidyl ethers according to the invention wherein n is above 1 may find a use for coatings, laminating, or as an adhesive.

Diglycidyl ethers according to the invention may for many purposes be mixed with other polyepoxides, for example with the conventional diglycidyl ethers of 2,2-bis(4-hydroxyphenyl)propane.

The following examples are given to illustrate the preparation of the instant diglycidyl ethers and their cure. It is understood that the examples are embodiments only and are given for the purpose of illustration only and the invention is not to be regarded as limited to any specific components and/or specific conditions recited therein. Unless otherwise indicated, parts and percentages are by weight.

EXAMPLE I

Preparation of diphenylol heptane

Phenol (2820 g; 30 moles) is melted, and saturated with gaseous HCl at 50° C. with vigorous stirring during 15 minutes (HCl content: 1% w). n-Heptanal (228 g; 2 moles) is added in 15 minutes under a slight $N_2$-stream. The temperature rose from 50° C. to 60° C. The mixture was stirred during a further 15 minutes at 50°–60° C.

Water, HCl and the excess of phenol were removed by vacuum distillation: first at 15 mm Hg at up to 80° C. where the bulk of phenol comes over, followed by vacuum steam distillation (75 mm Hg, bottom temperature 120° C.), and finally under $N_2$ (40 mm Hg, bottom temperature 140° C.).

The residue (535 g), crude 1,1-diphenylol heptane (DPH), contained HPL chromatography):

| | |
|---|---|
| para,para'-isomer | 56% w |
| ortho,para'-isomer | 37% w |
| ortho,ortho'-isomer | negligible |
| polyphenols (trimers) | 6% w |
| unidentified | 1% w |

Phenolic hydroxyl content: 0.68 eq./100 g (calculated: 0.70).

EXAMPLE II

Preparation of diglycidyl ether of DPH; method A

Crude diphenylol heptane from Example I (113.6 g; 0.772 phenolic hydroxyl equivalent) was dissolved in a mixture of epichlorohydrin (444 g; 4.8 mol.), i-propyl alcohol (259 g) and water (64.8 g). The solution was heated to 45° C., and aqueous sodium hydroxide (160 g of a 20% w solution; 0.8 mol. NaOH) was added gradually in 40 minutes with stirring. The temperature rose to 50° C. The mixture was kept at 60° C. during a further 20 minutes with stirring, then the stirrer was turned off. The mixture separated immediately into two phases, and the lower phase, a weakly alkaline sodium chloride solution, was drained off. Aqueous sodium hydroxide (40 g of the 20% w solution; 0.2 mol. NaOH) was added again, and the mixture was stirred vigorously for 5 minutes at 60° C. The stirrer was turned off, the alkaline aqueous phase—the lower layer—was drained off. The organic phase was washed consecutively with water (160 ml), 2% w aqueous $NaH_2PO_4$ (160 ml) and water (160 ml). Solvent and excess epichlorohydrin were distilled off; the last traces were removed by vacuum distillation and steam vacuum distillation as in Example I.

The glycidyl ether, a pale liquid (150 g) had the properties:

| | | |
|---|---|---|
| epoxy molar mass | 213 | (calculated 203) |
| viscosity (25° C.) | 2.9 | Pa.s |
| saponifiable chlorine | 250 | mg/kg |
| alpha-glycol | 15 | mmol./kg |
| phenolic hydroxyl | 11 | mmol./kg |

EXAMPLE III

Preparation of diglycidyl ether of DPH; method B

In a 5-liter round-bottom flask provided with stirrer, thermometer, and Dean & Stark reflux unit DPH, (568 g; 3.86 phenolic hydroxyl equivalent) was dissolved in epichlorohydrin (1850 g; 20 mol.), containing water (18.5 g) and tetramethylammonium chloride (2.19 g of a 50% w aqueous solution). The mixture was heated to 60° C., and gradual addition of sodium hydroxide (3.90 mol., as a 50% w aqueous solution) started according to the scheme:

- add 0.5% w of total amount in 15 minutes; temperature rises to 102° C.;
- add 1% w of total amount in 15 minutes; keep temperature at 102°–104° C.;
- add the rest in 150 minutes, and keep temperature at 102° C.

Reflux of epichlorohydrin/water starts at 102° C. The water was separated and the epichlorohydrin returned to the reactor. After addition of the NaOH the mixture was kept for 5 minutes at 102° C., the remaining epichlorohydrin was distilled off (the last traces in vacuum), the residue heated with dilute aqueous alkali (800 ml; 2.75% w NaOH) at 108° C., the mixture diluted with toluence (1200 ml), the aqueous phase separated, and the organic phase washed with a dilute phosphate solution (1800 ml; 2% w $NaH_2PO_4$), and the toluene removed in vaccum.

The glycidyl ether, a pale liquid (750 g) had the following properties:

| | | |
|---|---|---|
| epoxy molar mass | 214 | |
| viscosity (25° C.) | 3.0 | Pa.s |
| saponifiable chlorine | 70 | mg/kg |
| alpha-glycol | 19 | mmol./kg |
| phenolic hydroxyl | <10 | mmol./kg |
| solubility (% w) of | | |
| n-heptane | 13 | |
| white spirit (b.p. 140–165° C.) | 20 | |
| spirit (b.p. 184–211° C.; | | |
| <0.5% w aromatic) | >6 | |
| viscosity of the diglycidyl ether | | |
| diluted with 5% w of spirit | 1 | Pa.s (25° C.) |

It should be noted that the commercial diglycidyl ether of 2,2-bis(4-hydroxyphenyl)propane could not be diluted with any of these aliphatic solvents.

EXAMPLE IV

Cure with polyamines in solventless coating formulations

Polyether H: diglycidylether of DPH having epoxy molar mass 219.

Polyether A: diglycidylether of 2,2-bis(4-hydroxyphenyl)propane having epoxy molar mass 195.

Amine 15: adduct of diaminodiphenylmethane and epoxides; the adduct had on average 3.8 NH-functions per molecule and was diluted with solvent and accelerator. Amount to react with 1 mol. epoxide: 115 g.

| Formulations (parts by weight): | | |
|---|---|---|
| Polyether | H | A |
| | 100 | 100 |
| red iron oxide | 15 | 15 |
| asbestine | 15 | 15 |
| microtalc | 10 | 10 |
| Amine 15 | 55 | 60 |

The formulation with Polyether A is for comparative purposes only; the properties of the cured films are given between brackets in the Table below.

The formulations were sprayed onto degreased steel panels (paint films about 200 micrometers thick) and cured for 1 week at 10° C. or at room temperature (20° C.) Properties of the cured glossy films were:

| Cured at | 10° C. | 20° C. |
|---|---|---|
| Hardness (Buchholz) | 90 (100) | 100 (115) |
| Erichsen slow penetration (mm) | 7 (0.5) | 4.5 (1) |
| Impact resistance (cm.kg) direct | 11 (2) | 12.5 (7) |
| Resistance to aqueous: | | |
| formic acid (5% w) 2 weeks | u (u) | u (u) |
| $H_2SO_4$ (5% w) 8 weeks | u (u) | u (u) |
| NaOH (5% w) 5 weeks | u (u) | u (u) |
| Resistance to water at 70° C. | | |
| (8 weeks) | u (u) | u (u) |
| Resistance to xylene at 20° C. | u (u) | u (u) |
| Salt spray (10 days) | | |
| (mm from scratch) | 2 (3) | 2 (2) |
| Humidity (7 weeks) | + (+) | + (+) | u = unaffected
+ = resistance good

What is claimed is:

1. A diglycidyl ether of isomeric diphenylol alkanes having the formula:

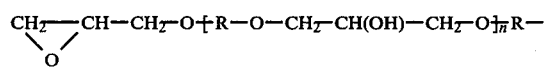

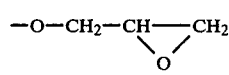

wherein n is a number of from about 0 to about 4, R is the group:

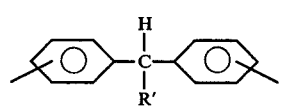

and R' is n-hexyl, the weight ratio of para,para'-isomer to ortho,para'-isomer being from 80:20 to 40:60.

2. The diglycidyl ether of claim 1 wherein n is a number of from 0 to 1.

3. In a process for the preparation of a diglycidyl ether by reaction of a diphenylol alkane with epichlorohydrin and alkali metal hydroxide, the improvement comprising the use of a phenol consisting essentially of a mixture of isomers of 1,1-bis(hydroxyphenyl)heptane, wherein the weight ratio of para,para'-isomer and ortho, para'-isomer is from about 80:20 to about 40:60.

4. A process for curing diglycidyl ether of claim 1 or 2 comprising mixing and reacting the diglycidyl ether with an epoxy resin curing agent.

5. The process of claim 4 wherein the epoxy resin curing agent is selected from the group consisting of an amino compound having at least two amino hydrogen functions per molecule, a polycarboxylic acid, and a polycarboxylic acid anhydride.

* * * * *